United States Patent
Koh

(10) Patent No.: US 7,223,244 B1
(45) Date of Patent: May 29, 2007

(54) SYSTEM AND METHOD FOR MONITORING HYPERCAPNIC VENTILATORY RESPONSE

(75) Inventor: Steve Koh, South Pasadena, CA (US)

(73) Assignee: Pacesetter, Inc., Sylmar, CA (US)

( * ) Notice: Subject to any disclaimer, the term of this patent is extended or adjusted under 35 U.S.C. 154(b) by 393 days.

(21) Appl. No.: 10/849,066

(22) Filed: May 18, 2004

(51) Int. Cl.
*A61B 5/205* (2006.01)

(52) U.S. Cl. ....................... 600/532; 600/508

(58) Field of Classification Search ............ 607/17–18, 607/20
See application file for complete search history.

(56) References Cited

U.S. PATENT DOCUMENTS

| | | | |
|---|---|---|---|
| 4,440,177 A | 4/1984 | Anderson et al. ........... 128/719 |
| 4,712,555 A | 12/1987 | Thornander et al. .. 128/419 PG |
| 4,716,887 A | 1/1988 | Koning et al. ........ 128/419 PG |
| 4,816,131 A | 3/1989 | Bomsztyk ................... 204/403 |
| 4,940,052 A | 7/1990 | Mann et al. .......... 128/419 PG |
| 4,944,298 A | 7/1990 | Sholder ................ 128/419 PG |
| 5,309,921 A * | 5/1994 | Kisner et al. ............... 600/532 |
| 5,318,597 A | 6/1994 | Hauck et al. ................. 607/20 |
| 5,466,254 A | 11/1995 | Helland ....................... 607/123 |
| 5,476,483 A | 12/1995 | Bornzin et al. ............... 607/17 |
| 5,540,727 A * | 7/1996 | Tockman et al. ............. 607/18 |
| 5,836,988 A | 11/1998 | Cooper et al. ................ 607/19 |
| 6,128,534 A | 10/2000 | Park et al. .................... 607/17 |
| 6,904,320 B2 * | 6/2005 | Park et al. .................... 607/17 |
| 6,928,324 B2 * | 8/2005 | Park et al. .................... 607/20 |
| 7,070,569 B2 * | 7/2006 | Heinonen et al. ........... 600/532 |
| 7,070,570 B2 * | 7/2006 | Sanderson et al. .......... 600/532 |
| 2004/0077953 A1 * | 4/2004 | Turcott ....................... 600/483 |

* cited by examiner

*Primary Examiner*—Carl Layno

(57) ABSTRACT

An exemplary method includes determining a parameter related to $CO_2$ concentration in a patient's blood, as well as determining a parameter related to respiration of the patient. The parameters are then processed to diagnose a cardiac condition based at least in part on the parameters.

30 Claims, 6 Drawing Sheets

SYSTEM AND METHOD FOR MONITORING HYPERCAPNIC VENTILATORY RESPONSE

TECHNICAL FIELD

The present invention generally relates to devices, systems and/or methods for diagnosing a patient's cardiac condition, and/or for providing cardiac pacing therapy. More particularly, various exemplary methods and systems determine one or more parameters related to patient breathing and use such information for diagnostics and/or therapy.

BACKGROUND

Congestive heart failure (CHF) is a condition that is often associated with a weakened heart that cannot pump enough blood to body organs. For example, as pumping action is lost, blood may back up into the heart and other areas of the body, including the liver, gastrointestinal tract, extremities and/or lungs. Implantable cardiac therapy devices are often used to overcome the deleterious effects caused by CHF, and in some cases to reverse the negative remodeling of the heart. Some implantable cardiac devices can also be programmed to compensate for worsening stages of CHF. For example, as CHF progresses, the myocardium weakens, which typically results in an increased left ventricular volume, also referred to as left ventricular dysfunction (LVD). To compensate for the increase in volume, a clinician may periodically measure a patient's left ventricular diameter, or another parameter associated with cardiac geometry, and program the implanted cardiac therapy device accordingly. This technique, however, requires clinical intervention, which consumes time and resources.

Some patients suffer from both congestive heart failure (CHF) and Cheyne-Stokes Respiration (CSR), which is defined as abnormal respiration in which periods of shallow/apneic breathing and deep breathing alternate (also known as periodic breathing). It has been found in studies that patients who suffer from both CHF and CSR tend to have larger left ventricular end-diastolic volumes (LVEDV), namely the volume of the left ventricle immediately prior to contraction of the left ventricle.

Lung and tissue gas stores of $CO_2$ affect the rapidity of the $CO_2$ exchange process from breathing, and thus have a direct influence on the respiratory control system damping. When the $CO_2$ stores are relatively large, fluctuations in ventilation exert a smaller effect on alveolar and arterial $PCO_2$ changes. Thus these gas stores act like a low-pass filter, attenuating the effect of rapid ventilatory fluctuations more than slow changes in ventilation.

As is well known, increased filling pressures (end-diastolic volume pressure) can lead to pulmonary vascular congestion and consequently, a decrease in pulmonary gas volume. This reduction in gas store will promote instability by elevating plant gain in the lung-chemoreflexor control. This gain is similar to hypercapnic ventilatory response slopes, which indicate the body's ability to expel $CO_2$ following a period of hypoventilation (abnormally slow and shallow respiration), which results in hypercapnia (high levels of $CO_2$ in the blood). It has also been discovered that hypercapnic ventilatory response among CHF patients with CSR is about double that compared to normal patients or those who suffer from obstructive sleep apnea.

What is needed is a reliable and convenient system and method that automatically determines progression and/or regression of heart failure, and that optionally can adjust patient therapy accordingly. Further, what is needed is a system that detects the rate at which $CO_2$ is expelled, and which uses that rate to detect progression of CHF, and/or to identify patients with CHF who are also likely have CSR.

SUMMARY

An exemplary method includes determining a $CO_2$-related value and a respiration-related value (e.g., tidal volume (TV)). The $CO_2$ and respiration values are compared to each other (in one embodiment, by calculating a ratio of $CO_2$ to TV), which provides an indication of a cardiac condition, such as a surrogate for heart failure progression and/or regression. The determined information may be used, for example, to warn the patient or a physician regarding progression of the heart failure condition, or to automatically adjust one or more operating parameters of the implanted cardiac device. Other exemplary methods, devices and/or systems are also disclosed.

In one embodiment, the comparison of $CO_2$ and respiration levels is in the form of the ratio of a $CO_2$ level to a respiration value, e.g. tidal volume. This ratio is a surrogate for hypercapnic ventilatory response, which may be used to detect various heart failure characteristics, such as LV dysfunction, LV end-diastolic volume or pressure, and the like. The ratio may also be used to detect pulmonary congestion, and to identify those patients who are more likely to suffer from CSR.

The various exemplary methods, devices and/or systems described herein, and equivalents thereof (e.g., structural and/or functional), are suitable for use in a variety of pacing therapies and other cardiac related therapies.

BRIEF DESCRIPTION OF THE DRAWINGS

Features and advantages of the described implementations can be more readily understood by reference to the following description taken in conjunction with the accompanying drawings.

DETAILED DESCRIPTION

The following description is not to be taken in a limiting sense, but rather is made merely for the purpose of describing the general principles of the illustrative embodiments. The scope of the described implementations should be ascertained with reference to the issued claims.

Exemplary Stimulation Device

The techniques described below are intended to be implemented in connection with any implantable monitoring and/or stimulating device that is configured for implant within a patient.

Figure 1:
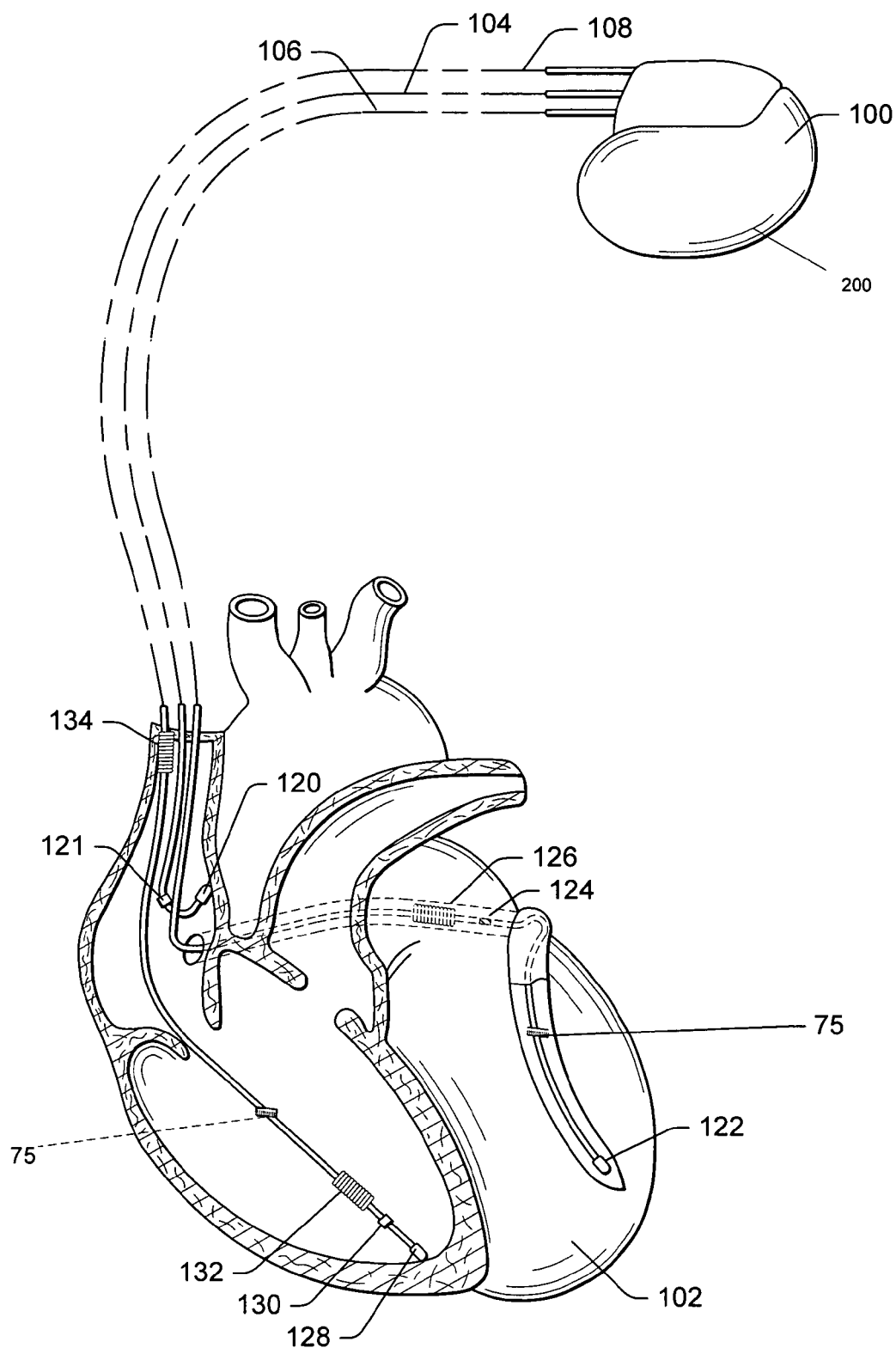
FIG. 1 is a simplified diagram illustrating an implantable stimulation device in electrical communication with at least three leads implanted into a patient's heart for sensing electrical activity and for delivering stimulation and/or shock therapy.

FIG. 1 shows an exemplary stimulation device 100 in electrical communication with a patient's heart 102 by way of three leads 104, 106, 108, suitable for generating potential fields, sensing potentials, and/or delivering stimulation and shock therapy. The right atrial lead 104, as the name implies, is positioned in and/or passes through a patient's right atrium. The right atrial lead 104 optionally generates a potential field (e.g., in combination with another electrode), senses atrial cardiac signals or other signals and/or provides right atrial chamber stimulation therapy. As shown in FIG. 1, the stimulation device 100 is coupled to implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well.

To generate a potential field; sense potentials, left atrial cardiac signals, and/or left ventricular cardiac signals; and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein. Electrodes are optionally positioned in or via such tributary veins.

Accordingly, an exemplary coronary sinus lead 106 is optionally designed to generate a potential field, sense potentials or signals and/or to deliver pacing therapy. For example, therapy may include left ventricular pacing therapy using at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of autonomic nerves.

Stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of generating potential fields, sensing potential and/or cardiac signals, and delivering stimulation in the form of pacing and shock therapy to the right ventricle. An exemplary right ventricular lead may also include at least one electrode capable of stimulating an autonomic nerve and/or anchoring the lead, such an electrode may be positioned on the lead or a bifurcation or leg of the lead.

Figure 2:
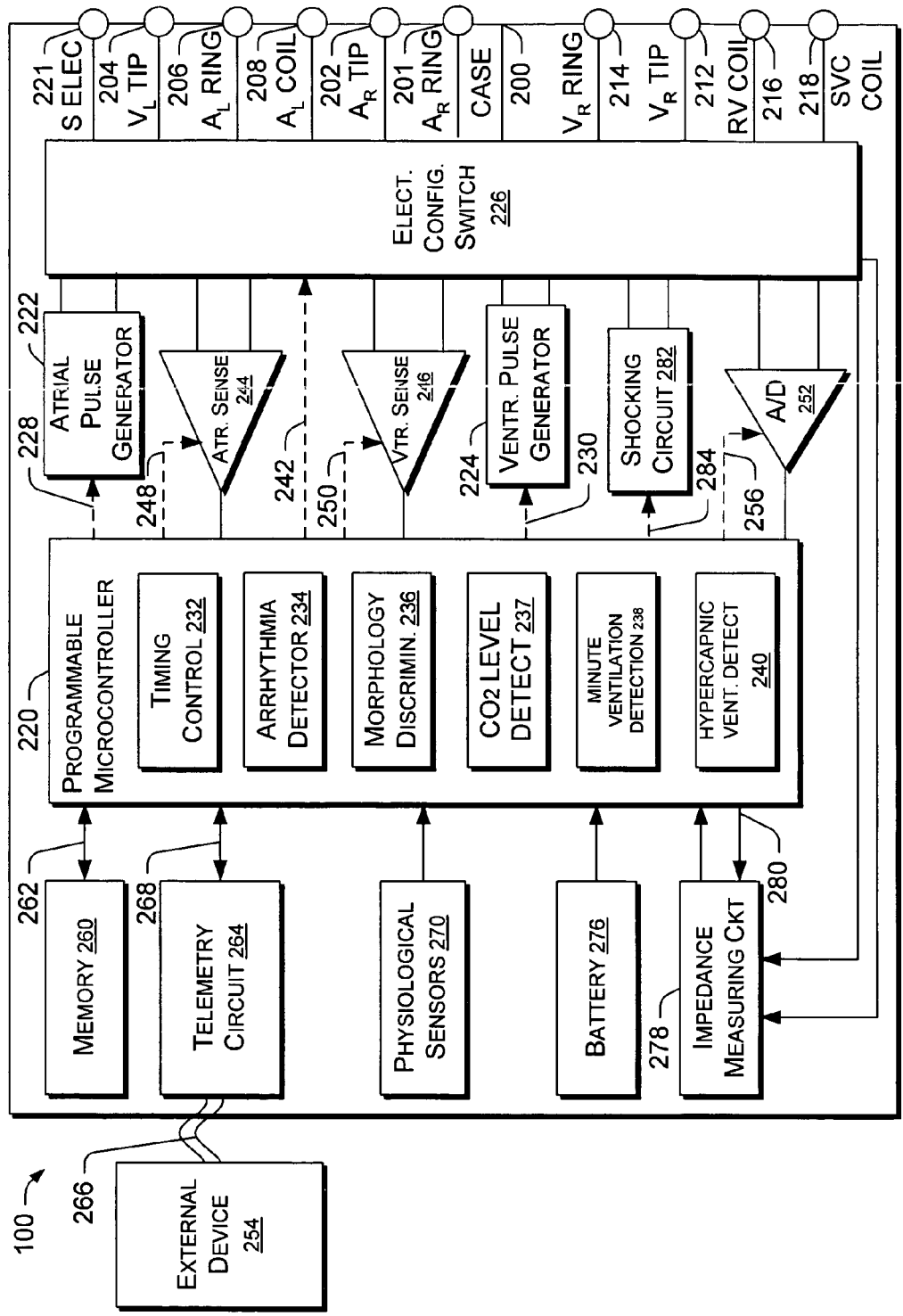
FIG. 2 is a functional block diagram of a multi-chamber implantable stimulation device illustrating basic elements that are configured to process sensed signals and respond accordingly.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques and methods described below can be implemented in connection with any suitably configured or configurable implantable device that can generate potential fields and/or sense potentials. Accordingly, one of skill in the art could readily duplicate, eliminate, or disable the appropriate circuitry in any desired combination to provide a device capable of generating potential fields and/or sensing potentials, and optionally treating appropriate chamber(s) with cardioversion, defibrillation, and/or pacing stimulation.

Housing 200 for stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking purposes. Housing 200 further includes a connector (not shown) having a plurality of terminals 202, 204, 206, 208, 212, 214, 216, and 218 (shown schematically and, for convenience, the names of the electrodes to which they are connected are shown next to the terminals).

To achieve right atrial generating, sensing and/or pacing, the connector includes at least a right atrial tip terminal ($A_R$ TIP) 202 adapted for connection to the atrial tip electrode 120. To achieve left chamber generating, sensing, pacing, and/or shocking, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively.

To support right chamber generating, sensing, pacing, and/or shocking, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of operation. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that carries out the functions described herein. The use of microprocessor-based control circuits for performing timing and data analysis functions are well known in the art. As described herein, an implantable device includes potential field generating and potential field sensing capabilities, which are optionally controllable via a microcontroller.

Representative types of control circuitry that may be used in connection with various exemplary device and/or methods described herein can include aspects of the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals used within a typical stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate potential field and/or pacing stimulation pulses for delivery by the right atrial lead 104, the coronary sinus lead 106, and/or the right ventricular lead 108 via an electrode configuration switch 226. It is understood that in order to generate potential fields and/or to provide stimulation therapy in each of the four chambers of the heart, the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit potential field generation and/or stimulation pulses.

Microcontroller 220 further includes timing control circuitry 232 to control the timing of potential field generation, potential sensing and/or stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc.

Microcontroller 220 further includes an arrhythmia detector 234, a morphology detector 236, and in one embodiment a minute ventilation (MV) detection module 238 and CO2 level detection module 237. The aforementioned components may be implemented in hardware as part of the microcontroller 220, or as software/firmware instructions programmed into the device and executed on the microcontroller 220 during certain modes of operation.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of potential field generations, potential sensing and/or stimulation pulses (e.g., unipolar, bipolar, combipolar, etc.) by selectively closing the appropriate combination of switches (not shown).

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. In addition, such circuits are optionally used to sense potentials, for example, in a potential field. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of any sensed signal by selectively closing the appropriate switches. In this way, the clinician may program the sensing polarity independent of potential field generation and/or stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, to selectively sense the signal (or potential) of interest. The automatic gain control enables the device 100 to deal effectively with the difficult problem of sensing low amplitude signal characteristics associated with atrial or ventricular fibrillation.

The outputs of the atrial and ventricular sensing circuits 244 and 246 are connected to the microcontroller 220, which, in turn, is able to trigger or inhibit the pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246.

For arrhythmia detection, the device 100 utilizes the atrial and ventricular sensing circuits, 244 and 246, to sense cardiac signals to determine whether a rhythm is physiologic or pathologic. The timing intervals between sensed events (e.g., P-waves, R-waves, and depolarization signals associated with fibrillation which are sometimes referred to as "F-waves" or "Fib-waves") are then classified by the arrhythmia detector 234 of the microcontroller 220 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals and/or sensed potentials are also applied to inputs of an analog-to-digital (A/D) data acquisition system 252. The data acquisition system 252 is configured to acquire intracardiac electrogram (IEGM) signals and/or potentials, convert the raw analog data into a digital signal, and store the digital signals for later processing and/or telemetric transmission to an external device 254. The data acquisition system 252 is coupled to the right atrial lead 104, the coronary sinus lead 106, and the right ventricular lead 108 through the switch 226 to sample potentials and/or cardiac signals across any pair of desired electrodes (including can or case or other electrodes).

The microcontroller 220 is further coupled to a memory 260 by a suitable data/address bus 262, wherein the programmable operating parameters used by the microcontroller 220 are stored and modified, as required, in order to customize the operation of the implantable device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy. One feature is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGMs) and status information relating to the operation of the device 100 (as contained in the microcontroller 220 or memory 260) to be sent to the external device 254 through an established communication link 266.

The implantable device 100 can further include a physiologic sensor 270, commonly referred to as a "rate-responsive" sensor because it is typically used to adjust pacing stimulation rate according to the exercise state of the patient. However, the physiological sensor 270 may further be used to detect changes in cardiac output, changes in the physiological condition of the heart, or diurnal changes in activity (e.g., detecting sleep and wake states). Accordingly, the microcontroller 220 responds by adjusting the various pacing parameters (such as rate, AV Delay, V—V Delay, etc.) at which the atrial and ventricular pulse generators, 222 and 224, generate stimulation pulses.

While shown as being included within the implantable device 100, it is to be understood that the physiologic sensor 270 may also be external to the stimulation device 100, yet still be implanted within or carried by the patient. Examples of physiologic sensors that may be implemented in device 100 include known sensors that, for example, sense respiration, blood pH, $CO_2$ level, and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.) and U.S. Pat. No. 6,128,534 to Park et al., which patents are hereby incorporated by reference. Each of these patents is incorporated by reference herein. In one illustrative embodiment, a pH (or $CO_2$) sensor, respiration-related (MV) sensor, and activity sensor are all included in the system, as is described in more detail below.

In one embodiment, the physiological sensors 270 preferably include sensors to help detect movement of the patient. The physiological sensors 270 may include a position and/or activity sensor. Signals generated by the position and/or activity sensor are passed to the microcontroller 220 for analysis, as described in greater detail below. The microcontroller 220 monitors the signals for indications of the patient's position and activity status, such as whether the patient is climbing upstairs or descending downstairs or whether the patient has been lying down for an extended period of time, thereby indicating a prolonged rest or sleep state.

The implantable device additionally includes a battery 276 that provides operating power to all of the circuits shown in FIG. 2. For the implantable device 100, which may employ shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 276 also desirably has a predictable discharge characteristic so that elective replacement time can be detected.

The implantable device 100 can further include magnet detection circuitry (not shown), coupled to the microcontroller 220, to detect when a magnet is placed over the implantable device 100. A magnet may be used by a clinician to perform various test functions of the implantable device 100 and/or to signal the microcontroller 220 that the external programmer 254 is in place to receive or transmit data to the microcontroller 220 through the telemetry circuits 264.

The implantable device 100 further includes an impedance measuring circuit 278 that is enabled by the microcontroller 220 via a control signal 280. The impedance measuring circuit 278 measures an impedance value, which can be used as a surrogate for respiration (tidal volume or minute ventilation), as described in further detail below. The impedance measuring circuit 278 is preferably coupled to the switch 226 so that any desired electrode may be used, preferably electrodes that measure transthoracic impedance. Further aspects of impedance are described below, especially the ability to measure respiration (e.g., tidal volume) in connection with the illustrative embodiments below.

In the case where the implantable device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (up to 0.5 J), moderate (0.5 J to 10 J), or high energy (11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

Figure 3:
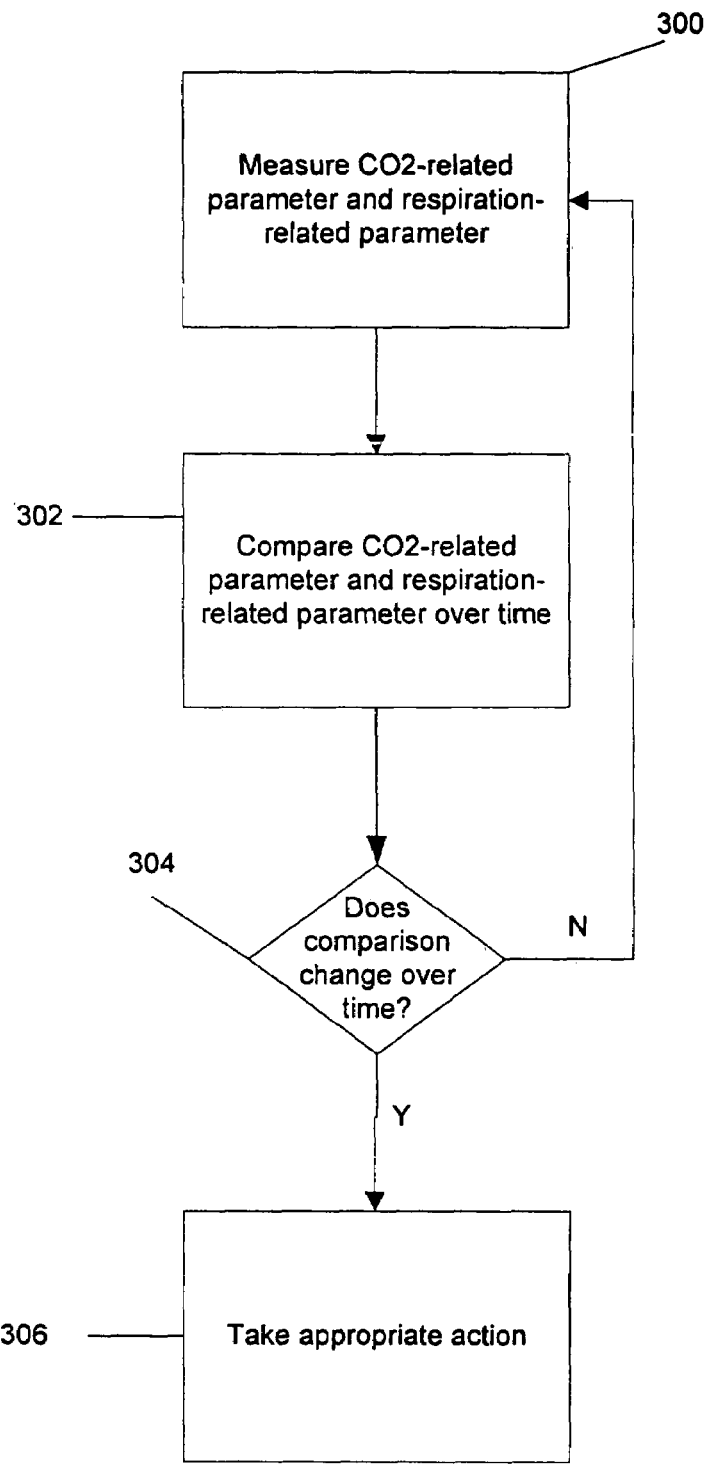
FIG. 3 is a flow diagram of an exemplary method for determining a surrogate for hypercapnic ventilatory response.

Hypercapnic Ventilatory Response as Indicator of Change in Physiologic Condition Various exemplary diagnostics and therapies will now be described. FIG. 3 shows an exemplary flow chart depicting one illustrative embodiment of a method for tracking a progression or regression of a physiologic condition, such as CHF, pulmonary congestion or edema, or detecting a patient who is likely to suffer from CSR.

According to the illustrative method shown in FIG. 3, operation commences at block 300, with device 100 measuring a $CO_2$-related parameter and a respiration-related parameter.

In one embodiment, a suitable sensor 75 (FIG. 1) is provided for measuring the $CO_2$-related parameter and preferably is, for example, a blood gas (e.g., $CO_2$) sensor, pH sensor, and the like. Examples of sensors that can be modified for use in the stimulation devices of the present invention are disclosed, for example, in U.S. Pat. No. 4,816,131 (Bomsztyk), and U.S. Pat. No. 4,716,887 to Konig et al., which are incorporated herein by reference. Suitable sensors and sensing techniques are well known to one of skill in the art and can be readily adapted for use in the present invention. Thus, in one embodiment the sensor 75 may detect $CO_2$ directly, or may be a pH sensor, and is connected to controller 220 via terminal 221, from which the $CO_2$ level in the patient's blood can be inferred by $CO_2$ detection module 237. In one illustrative embodiment, the sensor that measures the $CO_2$-related parameter is located on one of leads 104, 106, and 108, for example on the coronary sinus lead 106 (FIG. 1), to detect blood in the passage that returns deoxygenated blood from the capillaries of the heart; alternately, the $CO_2$ sensor can be located on the can 200, or on an additional lead (not shown) located within the patient's body for contact with blood. As is shown in FIG. 1, sensor 75 may be located on lead 106 and/or lead 108 (shown in dashed lines to represent potential alternate location for sensor 75), or any other suitable location, for example within the right atrium.

As described generally above, minute ventilation (also referred to as "minute volume" or "MV") is a respiratory-related parameter that is a measure of the volume of air inhaled and exhaled during a particular period of time. A minute ventilation signal can be obtained by measuring transthoracic (across the chest or thorax) impedance. Transthoracic impedance provides respiratory or ventilation information, including how fast and how deeply a patient is breathing. A component of transthoracic impedance varies as the patient inhales and exhales. Ventilation (e.g., breathing rate, which is also referred to as "ventilation rate" or "VR", and breathing volume, which is also referred to as "tidal volume" or "TV") information is included in the impedance signal, and is preferably used in the disclosed embodiments as described below. As is well known to those skilled in the art, the magnitude of the change of the impedance signal corresponds to the tidal volume and the frequency of change corresponds to respiration rate. Thus, by monitoring the amplitude of the impedance signal, the tidal volume value can be readily obtained.

A minute ventilation signal is derived from the impedance signal, as illustrated by Equation 1. MV measures air flow rate (e.g., liters per minute), TV measures volume per breath (e.g., liters per breath), and VR measures breathing rate (e.g., breaths per minute), as shown in the following equation:

$$MV = TV \times VR \quad (1)$$

By way of example, approaches for measuring transthoracic impedance are described in Hauck et al., U.S. Pat. No. 5,318,597 entitled "RATE ADAPTIVE CARDIAC RHYTHM MANAGEMENT DEVICE CONTROL ALGORITHM USING TRANS-THORACIC VENTILATION," assigned to the assignee of the present application, the disclosure of which is incorporated herein by reference; in U.S. Pat. No. 4,816,131 to Bomsztyk, and in U.S. Pat. No. 5,836,988 to Cooper et al., which are all incorporated herein by reference.

Referring again to FIG. 3, once the $CO_2$-related parameter and respiration-related parameter have been obtained, operation proceeds to block 302, and the $CO_2$-related parameter is compared with the respiration-related parameter. In one illustrative embodiment, a ratio of the $CO_2$-related value to the respiration-related value is computed, although other suitable comparisons may be used, which will be apparent to those skilled in the art. For example, the ratio of $CO_2$/TV may be used.

At query block 304, system 100 determines whether the comparison changes over time. In one embodiment, the ratio of $CO_2$/TV is periodically computed, e.g., daily, weekly, monthly, and the like. If, for example, the ratio increases over time, if it exceeds a preset threshold value, changes by more than a certain percent from an initial value, or changes by more than a certain percent from the previous value, then operation proceeds to block 306. If not, operation returns to block 300 to take the next measurement, which could be daily, weekly, monthly, or any other suitable interval between measurements.

If the comparison is positive at query block 304, operation proceeds to block 306, and the system 100 takes appropriate action. In one embodiment, system 100 may alert the patient through any well-known alert mechanism, thereby alerting the patient to seek medical help. Alternatively, system 100 may telemeter an alert via telemetry circuit 264 to external device 254, which may then transmit the alert transtelephonically, over a computer network, or the like, to the patient's physician. Moreover, in response to a positive result, the system 100 may change one or more operating parameters of the device, for example, implementing bi-ventricular pacing. In addition, system 100 may simply store the data and a suitable message for transfer to the physician during a subsequent follow-up interrogation of system 100.

Figure 4:
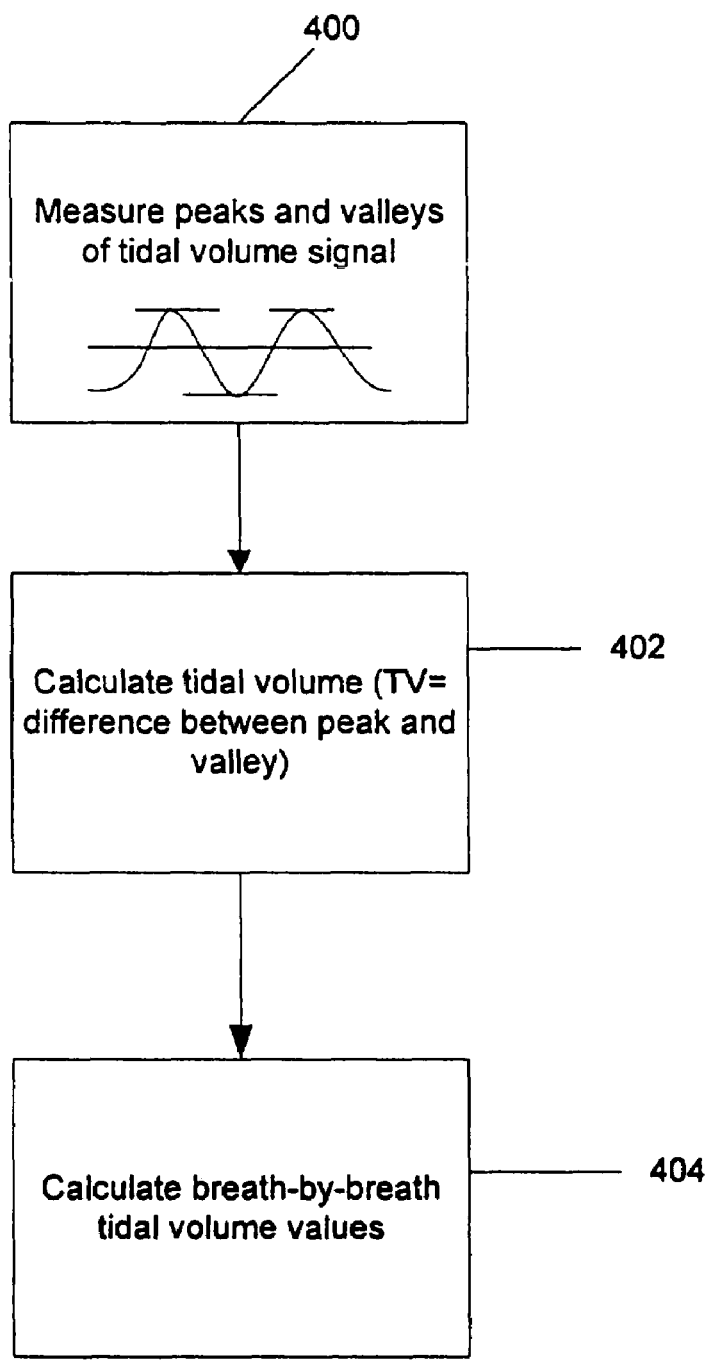
FIG. 4 is a flow diagram of an exemplary method for determining a tidal volume value.

FIG. 4 shows an exemplary flow diagram for calculating tidal volume values. At block 400, the peaks and valley of the tidal volume signal (as derived from the impedance signal) are measured. At block 402, the tidal volume is calculated as the difference between the peak and valley values (although other suitable measurements could be used as well, such as the magnitude of a rectified signal and the like). At block 404, tidal volume values are obtained for a plurality of breaths, to determine breath-by-breath tidal volume values, which are then used with corresponding $CO_2$ values to determine the $CO_2$/TV ratio values as described above.

Figure 5:
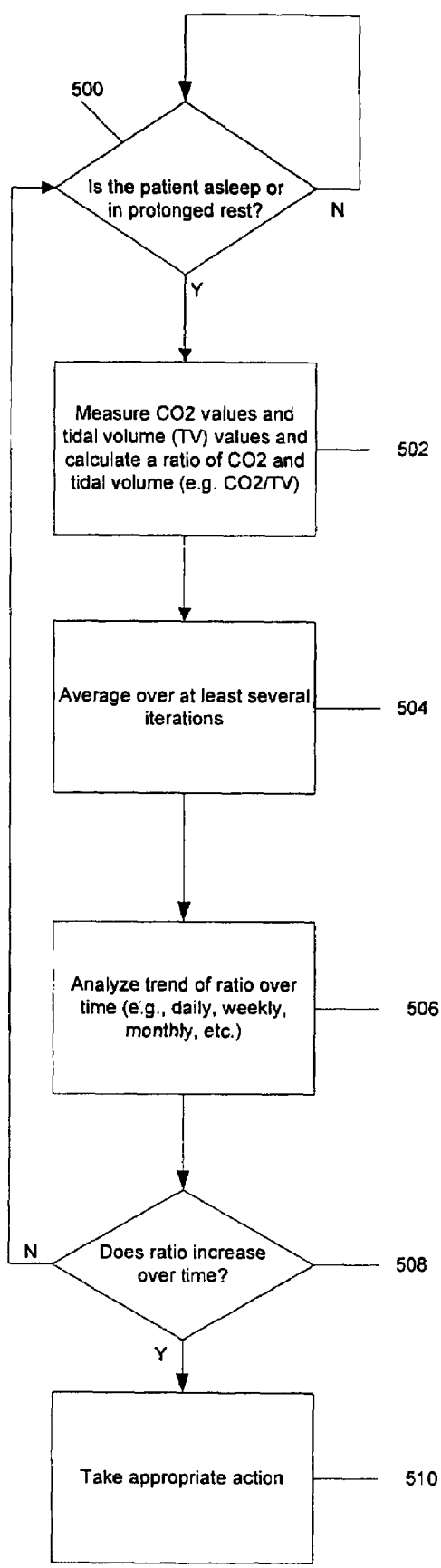
FIG. 5 is a detailed flow diagram of an exemplary method for determining the hypercapnic ventilatory response.

FIG. 5 shows a flow diagram of another illustrative embodiment for detecting progression of a physiologic condition. At query block 500, system 100 determines whether the patient is asleep or in a prolonged resting state. Preferably, this is determined by use of the activity sensor, for example by detecting low activity coupled with low activity variance, as described in the Bornzin patent cited above.

If the patient is asleep or in a prolonged rest state, operation proceeds to block 502, and system 100 detects both the $CO_2$ value and respiration-related value, preferably as described in detail above. Moreover, the ratio of $CO_2$/respiration-related value is computed. Operation proceeds to block 504, and the ratio is preferably averaged over at least several cycles. The value is then stored in memory.

At block 506, multiple ratio values, taken over an extended period of time (e.g., a day, a week, a month, etc.), are analyzed for any upward or downward trend in the data. For example, if the ratio increases by more than a preset percentage from the initial value (or from the previous value), or if the ratio exceeds a threshold value, then a potential change in a physiologic condition is indicated, such as progression of heart failure, pulmonary congestion, or an increased likelihood that a patient suffers from CSR. Thus, at query block 508, if the ratio increases overtime, operation proceeds to block 510 and appropriate action is taken. As described above, such action could be alerting the patient, alerting the patient's physician, adjusting one or more operating parameters of system 100, storing corresponding data to be retrieved during the next interrogation, and the like. It will also be apparent to those skilled in the art that if the ratio decreases over time, action can be taken, such as adjusting operating parameters, alerting the physician, and the like.

Figure 6:
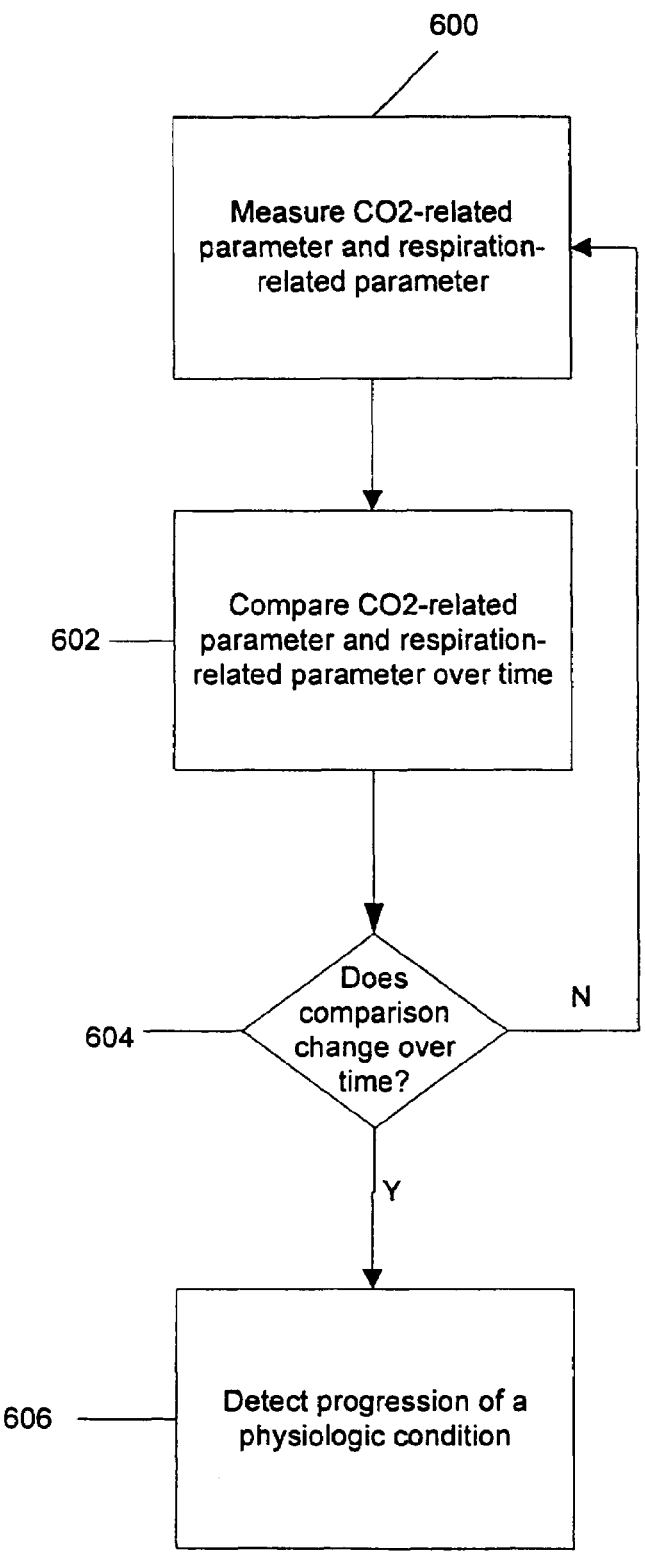
FIG. 6 is a flow diagram of an exemplary method for monitoring the hypercapnic ventilatory response to detect a change in a physiologic condition.

FIG. 6 shows an exemplary flow diagram of another illustrative embodiment. Operation begins at block 600, with system 100 measuring the $CO_2$-related parameter and respiration-related parameter as described in detail above. At block 602, system 100 compares the $CO_2$-related parameter with the respiration-related parameter over time. At query block 604, if the comparison changes over time (e.g., if a ratio increases by a preset percentage, or exceeds a threshold, etc.), operation proceeds to block 606, and system 100 detects a change in a physiologic condition, such as an increase in pulmonary congestion, which could lead to pulmonary edema. Preferably, system 100 will alert either the patient or physician, or both.

CONCLUSION

Although various exemplary devices and/or methods have been described in language specific to structural features and/or methodological acts, it is to be understood that the subject matter defined in the appended claims is not necessarily limited to the specific features or acts described. Rather, the specific features and acts are disclosed as exemplary forms of implementing the claimed subject matter.

What is claimed is:

1. A method comprising:
   determining a parameter related to $CO_2$ concentration in a patient's blood;
   determining a parameter related to respiration of the patient; and
   comparing the parameter related to $CO_2$ concentration to the parameter related to respiration to diagnose a physiologic condition based at least in part on the comparison of the parameters.

2. The method of claim 1 wherein determining a parameter related to $CO_2$ comprises determining a pH level of the patient's blood.

3. The method of claim 1, wherein determining a parameter related to $CO_2$ comprises determining the $CO_2$ level of the patient's blood.

4. The method of claim 1, wherein determining a parameter related to respiration comprises determining a tidal volume value.

5. The method of claim 4, wherein determining a tidal volume value comprises determining breath-by-breath tidal volume values.

6. The method of claim 1, wherein processing the parameters comprises calculating a ratio of the parameters.

7. The method of claim 6, wherein calculating the ratio comprises calculating a ratio of $CO_2$ to tidal volume.

8. The method of claim 1, wherein processing the parameters comprises diagnosing a heart failure condition.

9. The method of claim 1, wherein processing the parameters comprises analyzing the parameters over a period of time to detect a trend.

10. The method of claim 1, further comprising determining if the patient is inactive, and if the patient is not inactive, inhibiting the processing of the parameters.

11. The method of claim 1, and further comprising detecting a progression of heart failure based on the processing of the parameters, and changing an operating parameter in response to detecting a progression of heart failure.

12. The method of claim 1, wherein processing the parameters to diagnose a physiologic condition based at least in part on the parameters comprises diagnosing one of a progression of heart failure, pulmonary congestion, and an increased likelihood for Cheyne-Stokes Respiration (CSR).

13. An implantable device comprising:
   means for determining a parameter related to $CO_2$ concentration in a patient's blood;
   means for determining a parameter related to respiration of the patient; and
   means for comparing the parameter related to $CO_2$ concentration to the parameter related to respiration to diagnose a physiologic condition based at least in part on the comparison of the parameters.

14. The implantable device of claim 13 wherein the means for determining a parameter related to $CO_2$ comprises means for determining a pH level of the patient's blood.

15. The implantable device of claim 13, wherein the means for determining a parameter related to $CO_2$ comprises means for determining the $CO_2$ level of the patient's blood.

16. The implantable device of claim 13, wherein the means for determining a parameter related to respiration comprises means for determining a tidal volume value.

17. The implantable device of claim 13, wherein the means for processing the parameters comprises means for calculating a ratio of the parameters.

18. The implantable device of claim 13, wherein the means for processing the parameters comprises means for diagnosing a heart failure condition.

19. The implantable device of claim 13, wherein the means for determining a parameter related to respiration comprises means for determining breath-by-breath tidal volume values.

20. The implantable device of claim 13, wherein the means for processing the parameters comprises means for analyzing the parameters over a period of time to detect a trend.

21. The implantable device of claim 13, further comprising means for determining if the patient is inactive and means for inhibiting the processing of the parameters if the patient is not inactive.

22. The implantable device of claim 13, and further comprising means detecting a progression of heart failure based on the processing of the parameters, and means for changing an operating parameter in response to detecting a progression of heart failure.

23. An implantable cardiac system comprising:
   an implantable device comprising circuitry;
   one or more sensors configured for implant within the patient and in communication with the circuitry, wherein the one or more sensors are operative to sense a parameter related to a $CO_2$ level of the patient's blood and a parameter related to respiration of the patient; and
   wherein the circuitry is operative to compare the parameter related to the $CO_2$ level with the parameter related to respiration of the patient, and to detect a change in a physiologic condition based on the comparison.

24. The implantable cardiac system of claim 23 wherein the one or more sensors are operative to detect a pH level of the patient's blood.

25. The implantable cardiac system of claim 23, wherein the one or more sensors are operative to detect the $CO_2$ level of the patient's blood.

26. The implantable cardiac system of claim 23, wherein the one or more sensors are operative to detect a minute ventilation value.

27. The implantable cardiac system of claim 23, wherein the circuitry is operative to calculate a ratio of the $CO_2$ and respiration parameters.

28. The implantable cardiac system of claim 23, wherein the circuitry is operative to diagnose a heart failure condition based on a comparison of the parameter related to the $CO_2$ level with the parameter related to respiration of the patient.

29. The implantable cardiac system of claim 23, wherein the one or more sensors are operative to determine a tidal volume value.

30. The implantable cardiac system of claim 23, wherein the circuitry is operative to analyze the parameters over a period of time to detect a trend.

* * * * *